United States Patent [19]

Stanley

[11] Patent Number: 5,122,127
[45] Date of Patent: Jun. 16, 1992

[54] APPARATUS AND METHODS FOR USE IN ADMINISTERING MEDICAMENTS BY DIRECT MEDICAMENT CONTACT TO MUCOSAL TISSUES

[75] Inventor: Theodore H. Stanley, Salt Lake City, Utah

[73] Assignee: University of Utah, Salt Lake City, Utah

[21] Appl. No.: 403,743

[22] Filed: Sep. 5, 1989

Related U.S. Application Data

[63] Continuation-in-part of Ser. No. 60,045, Jun. 8, 1987, Pat. No. 4,863,737, which is a continuation-in-part of Ser. No. 729,301, May 1, 1985, Pat. No. 4,671,953.

[51] Int. Cl.$^5$ .............................................. A61K 9/22
[52] U.S. Cl. .............................. 604/890.1; 604/306; 424/435; 424/447
[58] Field of Search ................ 128/155, 156; 604/290, 604/303, 305, 306, 308, 303–309, 289, 890.1, 892.1; 424/434, 435, 443, 447–449

[56] References Cited

U.S. PATENT DOCUMENTS

| | | |
|---|---|---|
| D. 93,287 | 9/1934 | Reed . |
| 109,677 | 11/1870 | Seitz . |
| D. 117,455 | 11/1939 | Parr . |
| D. 117,456 | 11/1939 | Parr . |
| 747,525 | 12/1903 | Willis ................................. 604/289 |
| 802,190 | 10/1905 | Heineman ........................ 604/308 |
| 1,430,642 | 10/1922 | Gross . |
| 1,593,858 | 7/1926 | Venable . |
| 1,602,344 | 10/1926 | Eagle ................................. 604/304 |
| 1,847,415 | 3/1932 | Snell . |
| 1,915,614 | 6/1933 | Parker . |
| 1,971,560 | 8/1934 | Guyon ................................. 90/16 |
| 2,096,611 | 10/1937 | Ellestad ............................. 99/183 |
| 2,208,120 | 7/1940 | Coleman ........................... 107/82 |
| 2,246,778 | 6/1941 | Cahoon .............................. 99/138 |
| 2,295,042 | 9/1942 | Llewellyn .......................... 43/34 |
| 2,323,656 | 7/1943 | Helfenstein ....................... 43/36 |
| 2,388,533 | 11/1945 | Edmondson et al. ........... 128/202 |

(List continued on next page.)

FOREIGN PATENT DOCUMENTS

| | | |
|---|---|---|
| 0001907 | 5/1979 | European Pat. Off. . |
| 577563 | 6/1933 | Fed. Rep. of Germany ...... 604/289 |
| 2441341 | 6/1986 | France . |
| 132404 | 9/1978 | German Democratic Rep. . |
| 100714 | 8/1981 | Japan . |
| 118511 | 7/1982 | Japan . |
| 1083896 | 9/1967 | United Kingdom . |
| 1171691 | 11/1969 | United Kingdom . |
| 4108841 | 5/1983 | United Kingdom . |

OTHER PUBLICATIONS

Dyer, "Medicated Candies", 1 Q.S. 4 (1953).
Brown, "Absorption of Analgesics from the Buccal Mucous Membrane", 196, The Practitioner, 125 (1966).

(List continued on next page.)

*Primary Examiner*—C. Fred Rosenbaum
*Assistant Examiner*—Mark O. Polutta
*Attorney, Agent, or Firm*—Workman, Nydegger and Jensen

[57] ABSTRACT

Apparatus and methods for the dose-to-effect transmucosal administration of medicaments are disclosed. The present invention relates to such apparatus and methods which are useful in administering medicaments in a dose-to-effect manner such that sufficient drug is administered to produce precisely a desired effect. The invention also relates to an apparatus capable of placement directly on the patient's buccal mucosa having the capability of adjusting the drug surface area in direct contact with the mucosal tissue thereby enabling the proper amount of therapeutic agent or drug to be administered while accounting for individual needs and susceptibilities of the drug.

Through the use of selected permeation enhancers, the present invention enables lipophilic and nonlipophilic medicaments, which are not suitable for oral administration, to be rapidly administered noninvasively. Employing the present invention the drug may be introduced into the patient's bloodstream almost as fast as through injection, and much faster than using the oral administration route, while avoiding the negative aspects of both of these methods.

36 Claims, 7 Drawing Sheets

U.S. PATENT DOCUMENTS

| | | | |
|---|---|---|---|
| 2,469,589 | 5/1949 | Barricini | 99/138 |
| 2,488,272 | 11/1949 | Davis | 57/154 |
| 2,499,734 | 3/1950 | Edmondson et al. | 128/197 |
| 2,508,560 | 5/1950 | Adams | 43/36 |
| 2,553,446 | 5/1951 | Edmondson et al. | 128/188 |
| 2,807,262 | 9/1956 | Lew | 604/307 X |
| 2,857,908 | 10/1958 | Cornfield | 128/15 |
| 2,897,624 | 8/1959 | Yakel et al. | 43/36 |
| 2,915,061 | 12/1959 | Edmondson et al. | 128/188 |
| 2,926,121 | 2/1960 | Hobbs et al. | 424/440 |
| 2,963,404 | 12/1960 | Hammer et al. | 167/82 |
| 3,169,907 | 2/1965 | Heusser et al. | 424/440 X |
| 3,172,179 | 3/1965 | Schafer | 24/91 |
| 3,192,924 | 7/1965 | Edmondson et al. | 128/188 |
| 3,210,247 | 10/1965 | Suranyi | 514/270 |
| 3,264,115 | 8/1966 | Davis | 99/138 |
| 3,271,256 | 9/1966 | Frey | 167/82 |
| 3,341,414 | 9/1967 | Cherkas et al. | 167/82 |
| 3,344,030 | 9/1967 | Stevens et al. | 514/270 X |
| 3,367,332 | 2/1968 | Groves | 604/305 X |
| 3,399,673 | 9/1968 | Jones et al. | 128/188 |
| 3,418,743 | 12/1968 | Halvorsen | 43/35 |
| 3,429,308 | 2/1969 | Russell | 424/440 X |
| 3,493,652 | 2/1970 | Hartman | 424/435 X |
| 3,556,811 | 1/1971 | Smith | 99/134 |
| 3,797,494 | 3/1974 | Zaffaroni | 128/268 |
| 3,814,097 | 6/1974 | Ganderton et al. | 604/304 |
| 3,816,953 | 6/1974 | Hameen-Anttila | 43/35 |
| 3,867,927 | 2/1975 | Hergott | 128/15 |
| 3,943,268 | 3/1976 | Lariccia et al. | 128/260 |
| 3,996,934 | 12/1976 | Zaffaroni | 128/268 |
| 4,060,084 | 11/1977 | Chandrasekaran et al. | 128/260 |
| 4,093,709 | 6/1978 | Choi et al. | 424/19 |
| 4,131,648 | 12/1978 | Choi et al. | 424/22 |
| 4,138,344 | 2/1979 | Choi et al. | 252/1 |
| 4,139,627 | 2/1979 | Lane et al. | 424/267 |
| 4,168,308 | 9/1979 | Wretlind et al. | 514/270 X |
| 4,169,885 | 10/1979 | Raaf et al. | 424/440 |
| 4,226,848 | 10/1980 | Nagai et al. | 424/440 X |
| 4,292,299 | 9/1981 | Suzuki et al. | 424/440 X |
| 4,307,075 | 12/1981 | Martin | 424/28 |
| 4,341,208 | 7/1982 | Gordon et al. | 128/156 |
| 4,346,709 | 8/1982 | Schmitt | 128/260 |
| 4,372,942 | 2/1983 | Cimiluca | 424/16 |
| 4,390,520 | 6/1983 | Nagai et al. | 424/28 |
| 4,460,368 | 7/1984 | Allison et al. | 424/449 |
| 4,466,953 | 8/1984 | Keith et al. | 424/28 |
| 4,470,962 | 9/1984 | Keith et al. | 424/28 |
| 4,482,534 | 11/1984 | Blank | 424/28 |
| 4,485,087 | 11/1984 | Otsuka et al. | 424/28 |
| 4,517,173 | 5/1985 | Kizawa et al. | 424/435 |
| 4,529,589 | 7/1985 | Davydov et al. | 424/440 X |
| 4,551,329 | 11/1985 | Harris et al. | 424/22 |
| 4,572,832 | 2/1986 | Kigasawa et al. | 424/440 X |
| 4,573,996 | 3/1986 | Kwiatek et al. | 424/434 |
| 4,588,580 | 5/1986 | Gale et al. | 424/21 |
| 4,666,441 | 5/1987 | Andriola et al. | 604/897 |
| 4,671,953 | 6/1987 | Stanley et al. | 424/440 |
| 4,812,305 | 3/1989 | Vocal | 429/448 |
| 4,849,224 | 7/1989 | Chang et al. | 424/434 |
| 4,887,611 | 12/1989 | Rudiger et al. | 128/743 |
| 4,917,688 | 4/1990 | Nelson et al. | 604/306 |

OTHER PUBLICATIONS

Beckett et al., "Buccal Absorption of Basic Drugs and Its Application as an In Vivo Model of Passive Drug Transfer Through Lipid Membrands", 19, J. Pharm. Pharmac., 31S (1967).

Dearden et al., "Buccal Absorption as a Parameter of Analgesic Activity of Some P-Substituted Acetanilides", 23, Journal Pharm. Pharmac., 73S (1971).

Dearden et al., "A New Buccal Absorption Model", 23, J. Pharm. Pharmac., 68S (1971).

Dollery et al., "Differences in the Metabolism of Drugs Depending Upon Their Routes of Administration", 179, Annals of the New York Academy of Sciences, 108 (1971).

Dobkin, "Buprenorphine Hydrochloride: Determination of Analgesic Potency", 24, Canadian Anaesthesiology Society Journal, 186 (1977).

Edge et al., "Analgesic Effects of Sublingual Buprenorphine", 34, Anaesthesia, 463 (1979).

Fry, "Relief of Pain After Surgery", 34, Anaesthesia, 549 (1979).

Bullingham et al., "Sublingual Buprenorphine Used Postoperatively: Clinical Observations and Preliminary Pharmacokinetic Analysis", 12, Br. J. Clin. Pharmac., 117 (1981).

Hug et al., "The Pharmacokinetics of Fentanyl", Janssen Pharmaceutica Inc. (1981).

Ellis et al., "Pain Relief After Abdominal Surgery—A Comparison of I.M. Morphine, Sublingual Buprenorphine and Self-Administered I.V. Pethidine", 54, Br. J. Anaesth., 421 (1982).

Port et al., "Carfentanil: The Primate Experience", American College of Veterinary Anesthesiologist (1983).

Port et al., "Topical Narcotic Anesthesia", 59, Anesthesiology (1983).

Windholz et al., "The Merck Index", published by Merck & Co., Inc., pp. 575, 795, 796, and Appendix 3 (1983).

Abrams, "New Nitrate Delivery Systems: Buccal Nitroglycerin", vol. 105, American Heart Journal, pp. 848-854 (May 1983).

White et al., "Comparative Pharmacology of Intravenous Anesthetics—A Model for Determining Dosage Requirements and Therapeutic Concentration Ranges During Surgery", 59, Anesthesiology, A379 (Sep. 1983).

Asthana et al., "Verapamil Disposition and Effect on PQ-Intervals After Buccal, Oral and Intravenous Administration", Arzneim.—Forsch./Drug Res., pp. 498-502 (1984).

Derbyshire et al., "Non-Parenteral Postoperative Analgesia", Anesthesia, 39, pp. 324-328 (1984).

DeBoer et al., "Drug Absorption by Sublingual and Rectal Routes", 56, British Journal of Anaesthesiology, 69 (1984).

Stanley et al., "The Effect of Population Habits on Side Effects and Narcotic Requirements During High-Dose Fentanyl Anaesthesia", 31, Can. Anaesth. Soc. J., 398 (1984).

Bailey et al., "Anesthetic Induction with Fentanyl", 64, Anesth. Analg., 48 (1985).

Stanley et al., "Management of Pain and Pain-Related Problems in the Critically Ill Patient", in Critical Care, State of the Art, vol. 6 (1985).

Huttel et al., "Sublingual Flunitrazepam for Premedication", Acta Anaesthesiol Scand., 29, pp. 209-211 (1985).

Risbo et al., "Sublingual Buprenorphine for Premedication and Postoperative Pain Relief in Orthopedic Surgery", Acta Anaesthesiol Scand., 29, pp. 180-182 (1985).

Bell et al., "Buccal Morphine—A New Route for Analgesia?", The Lancet, 71 (1985).

Berry, "Premedication and Induction of the Different Child", (n.d.).

John F. Ryan, "Premedication, Induction and Parents", Newsletter, Boston, Mass. (n.d.).

"Sublimize (Fentanyl) as the Citrate Injection: Product Information", (n.d.).

Stanley, "Computer Control of Intravenous Anesthesia", 423.

Schechter et al., "Satus of Pediatric Pain Control: A Comparison of Hospital Analgesic Usage in Children and Adults", 77, Pediatrics, 11 (1986).

Prys-Roberts et al., "Pharmacokinetics of Anaesthesia", Preface.

Bailey et al., "Pharmacology of Intravenous Narcotic Anesthetics", in Anesthesia, 2nd ed. (Miller ed. 1986).

Su, "Intranasal Delivery of Peptides and Proteins", Pharmacy International (Jan. 1986).

Rothschild, "Are Sick Kids Treated Properly for Pain?", USA Today, Jan. 28, 1986.

Forbes et al., "2% Rectal Methohexital for Induction of Anesthesia in Children", vol. 65, Anesthesiology, No. 3, (Sep. 1986).

Newspaper Article entitled "Insulin Shots may soon be Replaced by a Nasal Spray", Friday, Sep. 26, 1986, (UPI).

"New Drugs/Drug News", Hospital Therapy, pp. 9, 10, and 15 (Nov. 1986).

Davis, "Parenteral Therapy Techniques-Abstracts", Hospital Pharmacy, vol. 21, pp. 1171-1178 (Dec. 1986).

"Personalized Dosing and Effective Drugs Can Control Emesis", Pharmacy Practice News, p. 11 (Mar. 1987).

"Adminstration of Drugs by the Buccal Route", The Lancet, pp. 666-667 (Mar. 21, 1987).

Lee, "Ophthalmic Delivery of Peptides and Proteins", Pharmaceutical Technology, pp. 26-38 (Apr. 1987).

Mecklenburg, "Insulin Pump Therapy 1987", Practical Diabetology, vol. 6, No. 2, pp. 1-7 (Mar./Apr. 1987).

Grover et al., "Low-Dose Intranasal Nitroglycerine Attenuates Pressor Response", 66, Anesthesiology, p. 722 (1987).

Oyama, Opioids in Anesthesia, Chapter 13: "Effects of Intrathecal and Epidural Morphine on Endocrine Function".

McLeskey, Opioids in Anesthesia, Chapter 20: "Continuous-Infusion Alfentanil for Surgical Anesthesia".

Kitahata, Opioids in Anesthesia, Chapter 28: "Intrathecal and Epidural Short-Acting Narcotics".

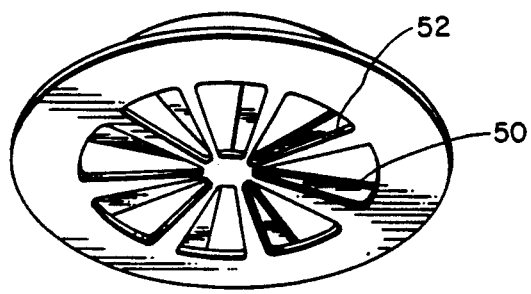
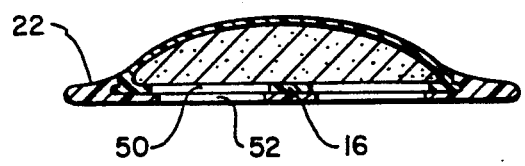
FIG. 13  FIG. 14
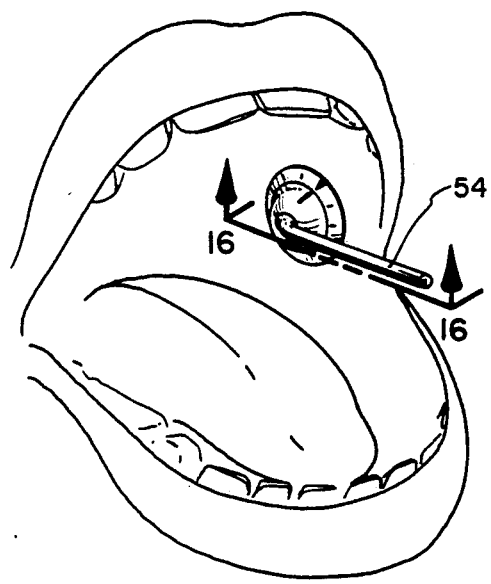
FIG. 15
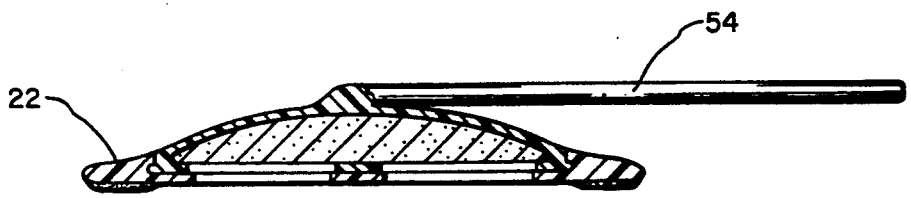
FIG. 16

APPARATUS AND METHODS FOR USE IN ADMINISTERING MEDICAMENTS BY DIRECT MEDICAMENT CONTACT TO MUCOSAL TISSUES

RELATED APPLICATIONS

This application is a continuation-in-part application of copending application Ser. No. 07/060,045, filed Jun. 8, 1987, in the names of Theodore H. Stanley, M.D. and Brian Hauge, and entitled "COMPOSITIONS AND METHODS OF MANUFACTURE OF COMPRESSED POWDER MEDICAMENTS," now U.S. Pat. No. 4,863,737 which issued Sep. 5, 1989, which is a continuation-in-part of application Ser. No. 06/729,301, filed May 1,1985, in the names of the inventors hereof, and entitled "METHODS AND COMPOSITIONS FOR NONINVASIVE ADMINISTRATION OF SEDATIVES, ANALGESICS, AND ANESTHETICS," now U.S. Pat. No. 4,671,953 which issued Jun. 9, 1987. The foregoing are incorporated herein by specific reference.

BACKGROUND

1. The Field of the Invention

The present invention relates to apparatus and methods for the dose-to-effect transmucosal administration of medicaments. More particularly, the present invention is directed to an adjustable apparatus and methods for noninvasive administration of precise amounts of medicaments through mucosal tissues by direct medicament contact to mucosal tissues.

2. The Background of the Invention

Recently, numerous advancements have taken place in the field of pharmacology an pharmaceutics with respect to the administration of drugs to treat various conditions. Despite the tremendous advancements in the field, however, drugs continue to be administered using substantially the same techniques that have been used for many decades. The vast majority of pharmaceutical agents continue to be administered either orally or by injection. Nevertheless, it is frequently found in the art that neither of these administration routes are effective in all cases, and both administration routes suffer from several disadvantages.

Oral administration is probably the most prevalent method of administering pharmacological medicaments. The medicament is generally incorporated into a tablet, capsule, or a liquid base, and then swallowed. The oral administration modality is often preferred because of its convenience. In addition, oral administration is generally nonthreatening, painless, and simple to accomplish for most patients.

Nevertheless, oral administration of drugs suffers from several disadvantages. One disadvantage is that pediatric and geriatric patients frequently have difficulty swallowing pills and other solid dosage forms, and such patients often refuse to cooperate in swallowing a liquid medication. In addition, for many medicaments, the act of swallowing the medicament often requires fluids and increases gastric volume and the likelihood of nausea and vomiting.

A further problem with oral administration is that the rate of absorption of the drug into the bloodstream after swallowing varies from patient to patient. The absorption of the drug is dependent upon the movement of the drug from the stomach to the small and large intestines, the effects of secretions from these organs, and on the resulting pH within the stomach and intestines. Anxiety and stress can dramatically reduce these movements and secretions, prevent or reduce the final effects of the drug, and delay onset of the drug's effects.

Most significant is the fact that there is normally a substantial delay between the time of oral administration and the time that the therapeutic effect of the drug begins. As mentioned above, the drug must pass through the gastrointestinal system in order to enter the bloodstream; this typically takes forty-five minutes or longer. As mentioned above, anxiety and stress often increase this delay. For many applications where immediate relief from pain or a serious medical condition or immediate effectiveness of the drug is required, this delay is unacceptable.

An additional disadvantage of oral administration is that many important therapeutic peptides and proteins are deactivated by the strong acidic environment and proteolytic enzymes in the gastrointestinal tract. Other drugs which are absorbed into the blood stream are almost immediately metabolized because the veins from the stomach and the small and large intestines pass directly through the liver. Thus, drugs entering the bloodstream must first pass through the liver before distribution into the general blood circulation. More than sixty percent of most drugs (and essentially one hundred percent of certain drugs) are removed from the patient's bloodstream during this "first pass" through the liver. The result is that oral administration is impractical for many drugs.

Further, additional stress is placed on the liver as it removes the excess drug from the bloodstream. This is particularly severe if the drug treatment has been occurring over an extended period of time. The liver may become overloaded with the drug's metabolite which then must be excreted. As a result, there is an increased risk of hepatic or renal disorders.

Another difficulty encountered in administering drugs orally is that dosages are prepared or determined for use with an "average" patient. Most drugs have widely varying effects on different patients. These effects depend upon patient habits, subtle genetic differences between patients, blood volumes, age, and numerous other known and unknown factors. Introducing a bolus of drug orally does not provide the ability to control the precise dose needed to obtain the desired effect, rather the dose is estimated in order to produce an average effect in an average patient. The result may be underdosing or overdosing a particular patient.

Underdosing a patient because of a low susceptibility to the drug fails to evoke the response sought by the physician. Overdosing the patient may dangerously affect vital body functions. Both underdosing and overdosing should be avoided.

In order to avoid some of the disadvantages of oral administration, injection is frequently used. Injecting a drug (generally intravenously or intramuscularly), results in rapid entry of the drug into the patient's bloodstream. In addition, this type of delivery avoids the removal of large quantities of the drug by the patient's liver. As a result, less total drug is usually needed compared to orally administered drugs. The drug instead becomes rapidly distributed to various portions of the patient's body before exposure to the liver.

Most patients, particularly children and geriatric adults, have an aversion to injections. In some patients, this aversion may be so pronounced as to make the use of injections a serious concern. Since intense psychological stress can exacerbate a patient's debilitated condition, it sometimes becomes undesirable to use injections where the patient is seriously ill or suffers from a debilitating condition or injury.

In addition, individual variations in susceptibility in the metabolism of various drugs (particularly drugs with central nervous system activity) are even more profound when utilizing the injection route. In many instances to prevent overdosing, it is the practice to inject a patient with a lower than average dose and then supplement the dose with additional injections as necessary. This "titration" makes necessary the use of repeated injections, which in turn greatly increases stress on the patient. Again, a precise dose cannot be administered to produce a precise effect because the patient's response varies widely depending on the specific characteristics of the specific patient.

Some investigators have suggested that it may be possible to administer medication through the buccal mucosa of the cheek pouch or by sublingual administration. See, U.S. Pat. No. 4,671,953 entitled "METHODS AND COMPOSITIONS FOR NONINVASIVE ADMINISTRATION OF SEDATIVES, ANALGESICS, AND ANESTHETICS." Such administration through the mucosal tissues of the mouth, pharynx, and esophagus of therapeutic drugs possesses a distinct usefulness. Administration of drugs by this route does not expose the drug to the gastric and intestinal digestive juices. In addition, the drugs largely bypass the liver on the first pass through the body, thereby avoiding additional metabolism and/or inactivation of the drug Generally the drugs which are administered by any of the methods described above have an unpleasant taste. As a result, in order to allow for buccal or sublingual administration through the oral mucosal tissues the drug is typically incorporated into some type of pleasant tasting mass, such as a "candy" matrix.

In the manufacture of conventional medicated candy products, the therapeutic agent is added to a molten candy mass. The resultant mixture is then thoroughly mixed to ensure proper distribution of the drug within the molten candy mass. The molten mixture is then poured into a mold cavity of desired size and shape and allowed to solidify into a solid mass.

For effective application of the drug, the final candy matrix may contain the drug uniformly distributed throughout in order to ensure uniform levels of medication. Alternatively, for some applications, varying concentrations within known and controlled ranges may be desired to vary the rate of drug administration. Difficulties are encountered in attempting to blend solid drugs in a uniform or otherwise carefully controlled manner. Many drugs are insoluble, or only partially soluble, in one or more of the ingredients of the hard candy base. Thus, the resultant product is often found to be lacking in uniform or controlled distribution of the drug.

In addition, it is often found that at the high temperatures needed to melt and form the candy mass, considerable decomposition of the medicament takes place. While the extent of decomposition may vary, high temperatures are generally undesirable in the handling and processing of medications. Thus, the formation process of prior art candy matrixes may itself degrade and/or inactivate the therapeutic agent.

Furthermore, many presently available medicated candy lozenges tend to crumble when placed in the mouth. As a result, uniform release of the drug into the mucosal tissues does not take place. Rather, the crumbled lozenge is mostly chewed, and swallowed, and the drug enters the bloodstream through the stomach and intestines as described above. Thus, it will be appreciated that candy lozenges have very definite limitations for use in the administration of a drug through the oral mucosal tissues. As a result, lozenges have not been used to administer potent, fast-acting drugs, such as drugs that affect the central nervous system, the respiratory system, the cardiovascular system, the renal vascular system, or other similar body systems.

While the administration of certain drugs through the oral mucosal tissues has shown promise, development of a fully acceptable method for producing a medication in a desirable form and administering the medication has been elusive. It has not been possible to develop an acceptable candy product for use with most drugs without heating the product to the point where degradation will be expected.

It should also be noted that pH conditions within the mouth may tend to adversely affect the administration of certain lipophilic and nonlipophilic drugs by the mucosal administration route. It has been found in the art that administration of drugs through the mucosal tissues generally occurs best when the drug is in the unionized form. Variations in pH affect the percentage of the drug which is unionized at a particular point in time. As a result, the pH conditions within the mouth can limit the effectiveness of certain drugs administered buccally or sublingually in that those conditions cause the drug to exist in the ionized form which is largely unavailable for transfer across the mucosal tissues.

Other medicaments are substantially nonlipophilic and do not naturally permeate mucosal tissues. Many important drugs, such as protein and peptide drugs having very large molecular weights and electrically charged functional groups, do not naturally permeate mucosal tissues. For example, insulin is a drug which must be administered intravenously, intramuscularly, or subcutaneously because it may not be administered orally without deactivation by the digestive system. In addition, insulin does not readily permeate mucosal tissues. Hence it would be a significant advancement in the art of drug administration to provide suitable apparatus and methods permitting the noninvasive, transmucosal administration of drugs which do not naturally permeate mucosal tissues and which are not suitable for oral administration.

It would be another important advancement in the art of administering medicaments, to provide apparatus and methods which deliver the precise dosage of the medicament to achieve a precise effect in every patient. A related advancement in the art would be to provide such apparatus and methods that avoid the disadvantages of overdosing, underdosing, and the immediate metabolism or inactivation of the digestive system, yet do not involve injection by needle into the patient.

It would also be an important advancement in the art to provide apparatus and methods for administering medicaments which do not subject the medicament to decomposition temperatures.

Such apparatus and methods of manufacture are disclosed and claimed herein.

BRIEF SUMMARY AND OBJECTS OF THE INVENTION

The present invention relates to apparatus and methods for the noninvasive administration of medicaments by direct medicament contact to mucosal tissues. The present invention includes apparatus and methods which are useful in administering drugs in a dose-to-effect manner such that sufficient drug is administered to produce precisely the desired effect. The invention also relates to apparatus and methods that enables both lipophilic and nonlipophilic (charged or uncharged) therapeutic agents to be administered transmucosally through the mucosal tissue of the mouth, thereby avoiding the problems of both injection and oral administration.

Employing the present invention, the drug may be introduced into the patient's bloodstream almost as fast as through injection, and much faster than using the oral administration route, while avoiding the negative aspects of both methods.

The present invention achieves these advantages by housing a medicament medium within an adjustable "dome" apparatus adapted to be placed directly on the mucosal tissues of the mouth. The "mucosal dome," can be used to administer medicaments in a dose-to-effect manner, or until the precise desired effect is achieved. The mucosal dome can then be removed from the patient's mouth or the drug administration rate may be adjusted.

Various mucosal dome configurations are possible within the scope of the present invention. Generally the mucosal dome includes a housing defining a medicament chamber therein. The medicament chamber encloses a medicament medium. The chamber has a base which defines at least one opening to the medicament chamber. The housing may take many different shapes; however, the housing should define a chamber for holding a quantity of medicament medium and provide an opening such that the medicament medium may be placed directly against the mucosal membrane.

The apparatus preferably includes means for temporarily positioning the housing against a mucosal membrane within the mouth in such a way that the opening to the medicament chamber is positioned adjacent the mucosal membrane. When the apparatus is properly positioned, the medicament within the medicament chamber is preferably capable of direct contact with the mucosal membrane.

The housing also includes means for adjusting the size of the opening to the medicament chamber. In this way the area of the medicament chamber opening, and consequently the area of medicament medium, in contact with the mucosal membrane may be adjusted. For example, depending on the configuration of the housing, the base of the housing will include a plurality of holes, perforations, slits, sectors, or other similar openings. A control member having a similar size and shape as the housing base and having an opening or openings corresponding to the openings of the housing base is preferably positioned adjacent the housing base. The control member is provided with means for moving the control member relative to the housing base such that the medicament medium surface area in contact with the mucosal membrane may be adjusted by sliding the control member relative to the housing base.

Other means for adjusting the size of the opening to the medicament chamber are also possible. For example, the medicament chamber base may be configured with a plurality of openings having removable covers. The covers are removed to expose the desired number of openings to provide a predetermined surface area of medicament medium exposure.

The medicament medium contained within the housing includes the desired medicament and in some cases, a permeation enhancer to improve the medicament permeability across the mucosal membrane. In most cases, the medicament is preferably soluble in the medium.

In another embodiment within the scope of the present invention, the medicament is preferably contained within the housing in a dry, powdered form. Access mean are provided for introducing a quantity of solvent into the chamber immediately prior to use, such that the medicament is dissolved in the solvent thereby forming a medicament medium. The ability to separate the drug from the solvent permits unstable drugs to be administered according to the present invention.

It may also be desirable to incorporate a handle or similar appliance onto the mucosal dome apparatus. A handle permits easy removal of the mucosal dome from the patient's mouth once the desired effect has been achieved. This is a substantial improvement over existing methods of administering drugs through the mucosal tissues of the mouth.

The present invention also provides the advantage of directly controlling the administration rate of the drug. This can be accomplished in a number of ways. First, the drug administration rate may be controlled by adjusting the contact surface area between the drug and the mucosal tissues. As will be discussed in greater detail below, the concentration of the drug within the mucosal dome also directly affects the administration rate. The drug administration rate may also be controlled chemically by selecting different permeation enhancers which alter the drug permeability across the mucosal membrane. In addition, the use of a rate controlling membrane between the medicament and mucosa, discussed in greater detail below, not only controls the administration rate, but also eliminates individual patient variations in administration rate.

A drug administered through the buccal tissues from a mucosal dome within the scope of the present invention will quickly enter the patient's bloodstream through the veins which serve those tissues. Appropriate monitoring of the patient's reaction to the drugs which have an observable or monitorable effect (such as a drug effecting the central nervous, cardiovascular, or renal vascular systems) will indicate when the drug has evoked a suitable response. The mucosal dome may then be removed, or the drug administration rate may be modified in order to maintain the desired effect.

It will be appreciated that the ever present risk of overdosing a patient is substantially minimized through the use of the present invention. The rate at which the drug is to be absorbed by the body can be varied by varying the administration rate as discussed above.

According to the present invention, the drug dose is given over a period of time rather than all at once, and the administration rate can be adjusted if it appears to be necessary. Once a sufficient drug response has been achieved, the patient can easily remove the mucosal dome from the patient's mouth.

It is, therefore, a primary object of the present invention to provide apparatus and methods for the noninvasive administration of medicaments to a patient in order to rapidly induce a desired systemic effect.

It is another object of the present invention to provide apparatus for administering medicaments which allow for precise control of the medicament dosage to achieve a precise effect of the drug to be administered.

An additional object of the present invention is to provide apparatus and methods for the noninvasive administration of medicaments to a patient that avoid the disadvantages of overdosing, underdosing, and the immediate metabolism or inactivation of the digestive system, yet do not involve injection by needle into the patient.

Yet another object of the present invention is to provide apparatus and methods for administering medicaments which do not subject the medicament to decomposition temperatures and which allow unstable medicaments to be used by separating the drug from the medicament medium solvent.

Still another object of the present invention is to provide apparatus and methods for administering medicaments which permit protein and peptide medicaments to be administered noninvasively and transmucosally.

These and other objects and features of the present invention will become more fully apparent from the following description and appended claims taken in conjunction with the accompanying drawings.

BRIEF DESCRIPTION OF THE DRAWINGS

FIG. 13 is a perspective view of yet another embodiment within the scope of the present invention.

FIG. 14 is a cross-sectional view of the embodiment illustrated in FIG. 13 taken along line 14—14.

FIG. 15 is a perspective view of yet another embodiment within the scope of the present invention positioned against a mucosal membrane within a patient's mouth.

FIG. 16 is a cross-sectional view of the embodiment illustrated in FIG. 15 taken along line 16—16.

DETAILED DESCRIPTION OF THE PREFERRED EMBODIMENTS

1. General Discussion

Figure 1:
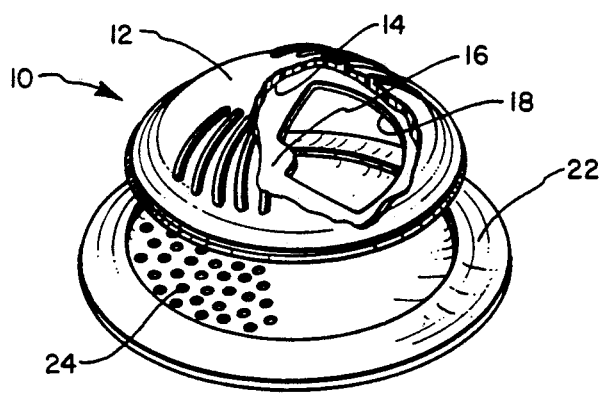
FIG. 1 is an exploded, cut-away perspective view of one embodiment within the scope of the present invention.

The present invention is related to apparatus and methods for the noninvasive transmucosal delivery of a medication in a dose-to-effect manner. Simply stated, the apparatus of the present invention relates to a housing capable of enclosing a quantity of therapeutic agent and capable of adhering to mucosal tissues of the mouth. The drug surface area in contact with the mucosal tissues may be adjusted. Since transmucosal drug delivery is proportional to the drug/mucosa interfacial area, adjusting the contact area adjusts the drug administration rate.

This particular method of delivery overcomes several of the limitations encountered in the delivery of drugs either orally or by injection. One of the primary advantages of the present invention is the ability to introduce drugs to a patient in a "dose-to-effect" manner. The drug is given to the patient until the precisely desired effect is obtained; this is in distinction to prior art methods where a predetermined quantity of the drug is introduced to the patient. Once the desired effect is obtained, the patient or the medical professional simply removes the mucosal dome from the patient's mouth or reduces the drug/mucosa interfacial surface area.

Not only does the contact surface area between the drug and the mucosal tissues affect the drug administration rate, but the concentration of the drug within the mucosal dome also directly affects the administration rate. The drug administration rate can also be controlled chemically. For example, the drug administration rate can be increased by incorporating a permeation enhancer with the drug which alters the drug's permeability across the mucosal membrane. In addition, the use of a rate controlling membrane between the medicament and mucosa not only controls the administration rate, but also eliminates individual patient variations in administration rate.

An important feature within the scope of the present invention is the ability to control the drug administration rate by using a rate limiting medium. It will be appreciated that the overall rate that a medicament diffuses through the mucosal membrane into the patient's blood stream depends upon the individual medicament permeabilities of the membranes or media that the medicament must pass through to enter the patient's blood stream. The overall medicament administration rate is determined by the net resistance of all diffusional components, the net diffusion being dominated by the single diffusion component with the lowest medicament permeability. Thus, if a rate limiting medium having a precise and reproducible low permeability is used, the overall medicament administration rate may be dominated by the rate limiting medium. Hence, the overall medicament administration rate may be maintained relatively constant despite variations in mucosal membrane permeability from person to person, time to time, and even position to position.

For instance, it is presently believed that the total amount of medicament which may be administered over time is lower if the medicament is incorporated into a hydrogel than if the medicament is free in solution. This suggests that medicament permeating from the hydrogel is a rate limiting step when compared to the permeation of medicament across the mucosal membrane. Therefore, the use of a hydrogel may provide a substantially uniform medicament permeation rate which is substantially independent of individual variations in mucosal membrane permeability.

Cellulose, including hydroxypropylcellulose and other cellulose derivatives known in the art, carbopol, gelatin, and other known substance which produce hydrogels may be used as part of the medicament medium within the scope of the present invention to provide a rate limiting function. It will be appreciated that other medicament media, such as creams, emulsions, suspensions, and other solid and semisolid media, besides hydrogels will also provide a rate limiting function. However, the medicament may not be as soluble in nonaqueous media. A sponge-like device saturated with medicament may also provide a suitable rate limiting function.

According to the present invention, a removable or nonremovable handle or other suitable appliance, may optionally be attached to the housing of the mucosal dome. Attaching the mucosal dome to a handle facilitates the administration of precise dosages. Once a particular effect is induced, the mucosal dome can be withdrawn using the handle as described above. In addition, the handle may facilitate adjusting the drug/mucosa interfacial surface area.

Placing a handle onto the mucosal dome also facilitates the temporary removal of medication for inspection or the reduction of the effect when necessary. Unlike administration of drugs orally or even sublingually, the present composition can easily be removed to assess the effect induced at any particular time. When a pill or lozenge is used, removal from the patient's mouth at an intermediate stage to assess effect is generally impractical, if not impossible.

Because the mucosal dome device within the scope of the present invention protects the medicament from the patient's saliva, the medicament is generally not free in the patient's saliva. Hence, medicament does not reach the taste buds in the patient's mouth. As a result, bitter tasting drugs are not noticed by the patient.

In addition, because the medicament is protected somewhat from the patient's saliva, the dilution and antibuffering affects of saliva do not significantly affect the medicament administration rate. Importantly, the medicament may be buffered within the medicament chamber at a pH which will maximize drug absorption.

Another important feature of the present invention is the incorporation of permeation enhancers within the medicament medium of the mucosal dome. Permeation enhancers may be selected to improve the mucosal membrane permeability to nonlipophilic and lipophilic drugs. The use of permeation enhancers will be discussed in greater detail below. Thus, the apparatus and methods within the scope of the present invention permit the use of both lipophilic and nonlipophilic drugs which do not naturally permeate the mucosal tissues of the mouth.

Added to the apparatus described above will be the appropriate therapeutic agent or medicament incorporated into a medicament medium. These include agents which affect the central nervous system, the cardiovascular system, the renal vascular system, body metabolism, or other body systems. Immediate systemic effects from central nervous system-acting drugs (such as sedation, anxiolysis, analgesia, amnesia, and anesthesia), cardiovascular-acting agents (such as antihypertensives and antianginal drugs), renal vascular-acting agents, and numerous other therapeutic agents can also be accomplished by employing the present invention.

2. Apparatus of the Present Invention

Various mucosal dome configurations are possible within the scope of the present invention. Generally, the mucosal dome within the scope of the present invention includes a housing which encloses a quantity of medicament medium. The housing may take many different shapes; however, the housing should define a medicament chamber for holding a quantity of medicament medium. The medicament chamber preferably includes a base which defines an opening to the medicament chamber. The medicament chamber base is preferably positioned adjacent a mucosal membrane within the patient's mouth. An adhesive material may be applied to the apparatus so that the medicament medium may be placed directly against a mucosal membrane within the mouth.

The housing also includes means for adjusting the surface area of the medicament chamber opening in contact with the mucosal membrane. For example, depending on the configuration of the housing and medicament chamber, the medicament chamber base will include a plurality of holes, perforations, slits, sectors, or other similar openings which combine to form the medicament chamber opening. A control member, having a similar size and shape as medicament chamber base and having an opening corresponding to the medicament chamber opening, is preferably positioned adjacent the medicament chamber base.

Means are preferably provided for moving the control member and the medicament chamber base relative to each other such that the interfacial surface area between medicament medium and the mucosal membrane may range from zero to a maximum area by such movement. Alternatively, the medicament medium surface area in contact with the mucosal membrane may be adjusted by removing covers over the medicament chamber opening.

Figures 2, 3:
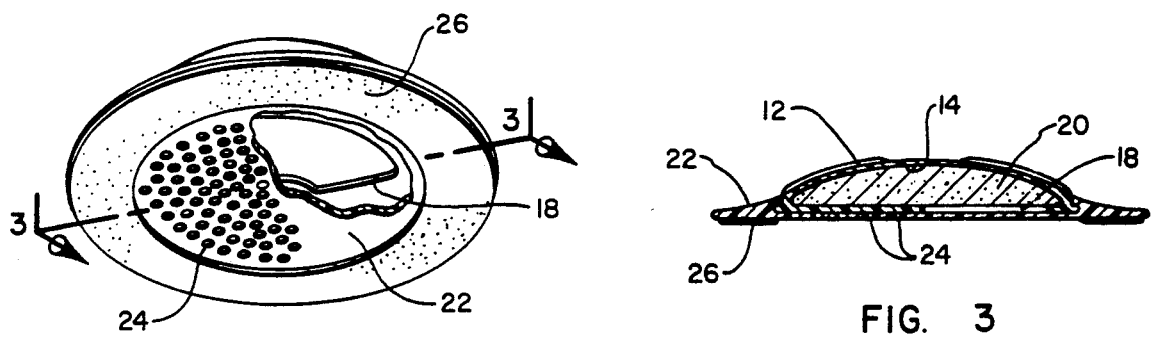
FIG. 2 is a perspective view of the embodiment illustrated in FIG. 1 viewing the medicament chamber base.
FIG. 3 is a cross-sectional view of the embodiment illustrated in FIG. 2 taken along line 3—3.

The figures illustrate several possible embodiments of the apparatus within the scope of the present invention. Reference is now made to the figures wherein like parts are identified by like numerals. In FIGS. 1—3, for example, mucosal dome 10 includes housing 12 which defines medicament chamber 14. The medicament chamber has a circular medicament chamber base 16 which defines a medicament chamber opening 18. A quantity of medicament medium 20 is located within the medicament chamber.

Disk-shaped control member 22 has a similar size as the medicament chamber base 16 and defines a plurality of openings 24 on one semicircle of the control member. Control member 22 is preferably positioned adjacent the medicament chamber base. An adhesive material 26, located on the control member, is provided so that the mucosal dome may be positioned adjacent a mucosal membrane within a patients mouth. Rotation of control member 22 relative to housing 12 either increases or decreases the effective area of medicament chamber opening 18 in contact with a mucosal membrane. This embodiment functions much like a salt or pepper shaker having perforations which may be opened or closed as desired.

Figure 4:
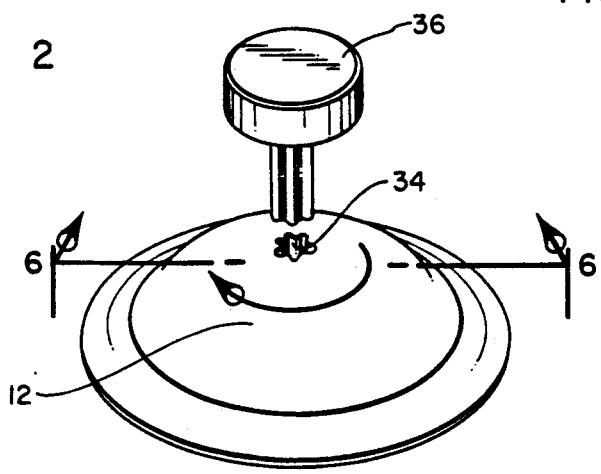
FIG. 4 is a perspective view of another embodiment within the scope of the present invention.
Figure 5:
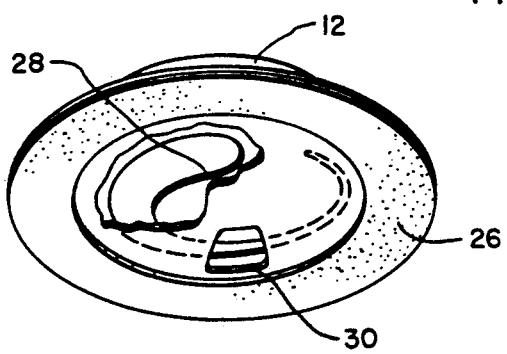
FIG. 5 is a perspective view of the embodiment illustrated in FIG. 4 viewing the medicament chamber base.
Figure 6:
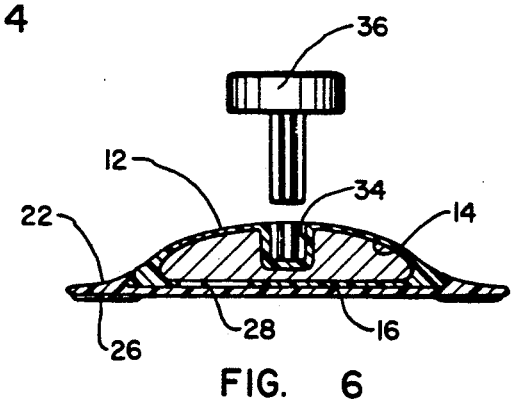
FIG. 6 is a cross-sectional view of the embodiment illustrated in FIG. 4 taken along line 6—6.
Figure 7:
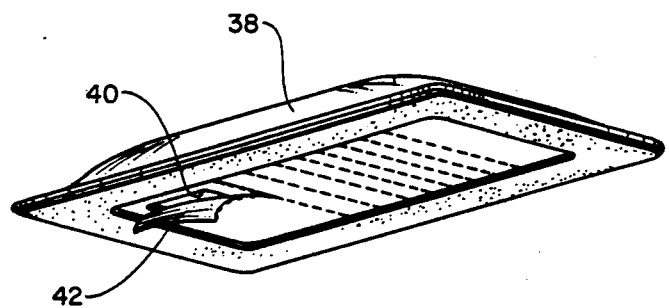
FIG. 7 is a perspective view of yet another embodiment within the scope of the present invention viewing the medicament chamber base.
Figure 8:
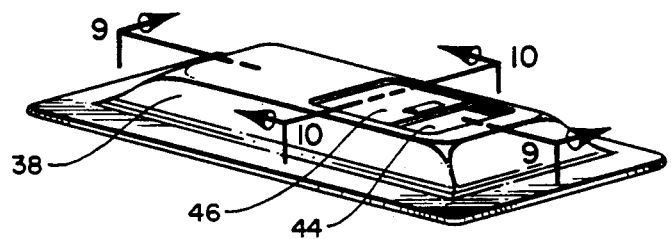
FIG. 8 is another perspective view of the embodiment illustrated in FIG. 7.
Figure 9:
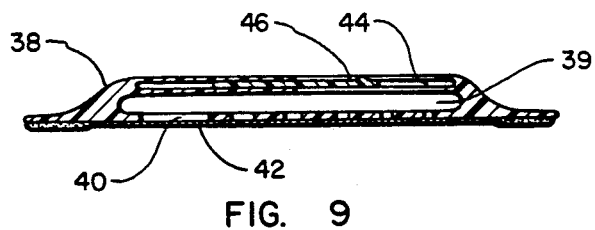
FIG. 9 is a cross-sectional view of the embodiment illustrated in FIG. 8 taken along line 9—9.
Figure 10:
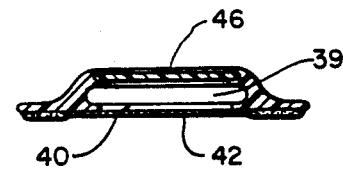
FIG. 10 is a cross-sectional view of the embodiment illustrated in FIG. 8 taken along line 10—10.

FIGS. 4-6 illustrates another possible mucosal dome embodiment capable of adjusting the surface area of the medicament medium in contact with the mucosal membrane. The mucosal dome includes a circular housing 12 which defines medicament chamber 14. The medicament chamber has a circular medicament chamber base 16 which defines a medicament chamber opening 28. Opening 28 is generally "C" shaped having a larger opening at one end which gradually tapers to a smaller opening at the other end. A quantity of medicament medium 20 is located within the medicament chamber.

A disk-shaped control member 22 has a similar size as the medicament chamber base 16 and defines an opening 30 on the control member. Control member 22 is preferably positioned adjacent the medicament chamber base. An adhesive material 26, located on the control member, is provided so that the mucosal dome may be positioned adjacent a mucosal membrane within a patient's mouth.

Housing 12 also defines a key hole 34 configured to accommodate a key 36. Rotation of key 36 within key hole 34 permits Rotation of control member 22 relative to housing 12. This action adjusts the effective area of medicament chamber opening 28 in contact with a mucosal membrane to an area in the range from zero to the maximum area provided.

FIGS. 7-10 illustrate yet another embodiment capable of adjusting the surface area of the medicament medium in contact with the mucosal membrane. This is accomplished by providing a housing 38 defining a medicament chamber capable of holding a quantity of medicament medium. The medicament chamber has a plurality of openings 40 which initially are covered with coverings 42. As coverings 42 are removed, the surface area of openings 40 capable of contact with the mucosal membrane may be adjusted from an area of zero to the maximum area provided by openings 40.

The embodiment illustrated in FIGS. 7-10 also includes an access port 44 to the medicament chamber. Lid 46 may be slid to open or close access port 44. In this way, medicament medium may be added or removed from the mucosal dome device. Access port 44 also permits unstable medicaments or dry, powdered medicaments to be stored in the medicament chamber and later combined with a pharmaceutically acceptable carrier or suitable solvent prior to use.

Figure 11:
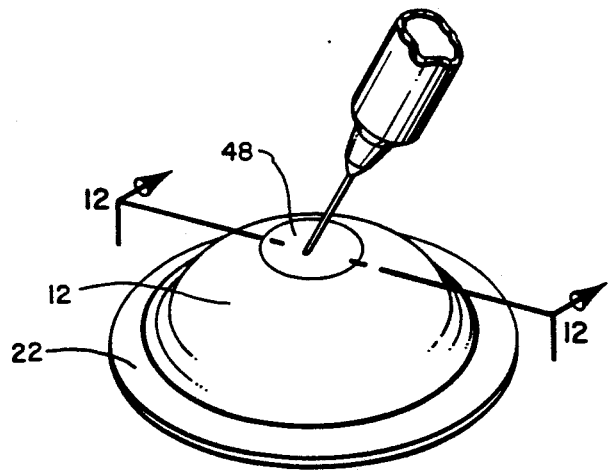
FIG. 11 is a perspective view of another embodiment within the scope of the present invention showing a penetrable septum for accessing the medicament chamber.
Figure 12:
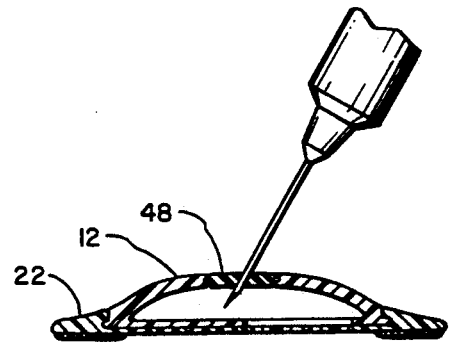
FIG. 12 is a cross sectional view of the embodiment illustrated in FIG. 11 taken along line 12—12.

FIGS. 11 and 12 illustrate yet another means for accessing the medicament chamber. The embodiment includes a penetrable septum 48 which may be pierced by a conventional hypodermic needle to withdraw or add medicament medium from the device. The embodiment shown in FIGS. 11 and 12 also permits unstable medicaments or dry, powdered medicaments to be stored in the device and later combined with a pharmaceutically acceptable carrier prior to use.

FIGS. 13 and 14 illustrate still another possible embodiment capable of adjusting the surface area of the medicament medium in contact with the mucosal membrane. The general apparatus is similar to that illustrated in FIGS. 1-3 above, except that the medicament chamber base 16 includes a plurality of pie-shaped sectors 50 around the circular medicament chamber base A disk-shaped control member 22 having a similar size as medicament chamber base 16 and having similarly shaped and spaced sectors 52 around the circular control member is preferably positioned adjacent the medicament chamber base. Rotating of the control member relative to the chamber base either opens or closes sectors 50 in contact with a patient's mucosal membrane.

It will be appreciated that there are many other possible embodiments within the scope of the present invention capable of adjusting the surface area of the medicament medium in contact with the mucosal membrane which are not specifically illustrated herein. However it is important that the configuration provide control over the medicament medium surface area in contact with the mucosal membrane.

The housing is preferably constructed of a material which is nontoxic, chemically stable, nonreactive with the medicament, the medicament medium, or any permeation enhancers used, and inexpensive. Possible construction materials include: polyethylene, polyolefins, polyamides, polycarbonates, vinyl polymers, and other similar materials known in the art.

The housing may also include flanges located about the periphery of the housing for receiving an adhesive so that the housing may be maintained in position against the mucosal membrane. The housing may also contain an access port through which medicament medium may be introduced into the housing or removed therefrom while the housing is positioned against the mucosal membrane.

As shown in FIGS. 15 and 16, a handle 54 or similar appliance may optionally be attached to the housing to facilitate placement and removal of the apparatus. The handle is particularly desirable to provide user-control of placement and removal and to maintain the housing in contact with the mucosal tissues of the mouth. The handle may also be used to adjust the surface area of the medicament medium in contact with the mucosal membrane.

The medicament medium contained within the housing includes the desired medicament and in some cases, a permeation enhancer to improve the medicament permeability across the mucosal membrane. In most cases, the medicament will be preferably soluble in the medium. Typical medicament media within the scope of the present invention include aqueous solutions, hydrogels, liquid fats, oils, waxes, creams, emulsions, suspensions, sponge-like materials, and gases or volatile liquids. It is important that the medicament medium be nontoxic to the mucosal membrane and chemically and physically stable (e.g., does not degrade and does not react with the medicament or with a permeation enhancer).

It can be seen, therefore, that the present invention provides a great deal of flexibility in the construction of an appropriate drug-administration apparatus. The quantity of drug contained in any mucosal dome can be varied within wide ranges, and both liquid and solid drug formulations may be used in the present invention. In addition, a suitable handle, optionally attached to the mucosal dome, provides a wide range of flexibility.

3. Mucosal Membrane Permeation Enhancers

As discussed above, many drugs are present in solution in both the unionized and ionized forms. Generally only lipid soluble or lipophilic drugs readily diffuse across mucosal membranes. However, it has been found that nonlipophilic drugs may diffuse across mucosal membranes if the mucosal membrane is treated with a permeation enhancer. It has also been found that certain permeability enhancers can significantly enhance the permeability of lipophilic and nonlipophilic drugs.

Typical permeation enhancers include bile salts such as sodium cholate, sodium glycocholate, sodium glycodeoxycholate, taurodeoxycholate, sodium deoxycholate, sodium lithocholate chenocholate, chenodeoxycholate, ursocholate, ursodeoxycholate, hyodeoxycholate, dehydrocholate, glycochenocholate, taurochenocholate, and taurochenodeoxycholate. Other permeation enhancers such as sodium dodecyl sulfate ("SDS"), dimethyl sulfoxide ("DMSO"), sodium lauryl sulfate, salts and other derivatives of saturated and unsaturated fatty acids, surfactants, bile salt analogs, derivatives of bile salts, or such synthetic permeation enhancers as described in U.S. Pat. No. 4,746,508 may also be used.

It is almost impossible to predict which enhancer will work best for a given drug. For each individual drug, only experiments can tell which enhancer is the most suitable. However, it is generally believed that bile salts are good enhancers for hydrophilic drugs and long chain fatty acids, their salts, derivatives, and analogs are more suitable for lipophilic drugs. DMSO, SDS, and medium chain fatty acids (C-8 to about C-14) their salts, derivatives, and analogs may work for both hydrophilic and lipophilic drugs.

The effectiveness of some enhancers may vary depending on the chemical compound to be permeated. One particular enhancer may work very well on one drug but may not have any effect on another drug. For example, oleic acid greatly improves the transdermal permeability of estradiol, a very lipophilic drug, but oleic acid does not have any effect on the transmucosal permeability of glucose, a very hydrophilic drug. Although it is possible to speculate whether a given enhancer may or may not enhance a given drug's permeability, the actual effectiveness of an enhancer should be verified experimentally.

The permeation enhancer concentration within the medicament medium may be varied depending on the potency of the enhancer. Other criteria for determining the enhancer concentration include the potency of the drug. The upper limit for enhancer concentration is set by toxic effect to or irritation limits of the mucosal membrane. The solubility of the enhancer within the medicament medium may also limit enhancer concentration.

The following is a list of typical enhancers and exemplary concentration ranges for each enhancer:

| Enhancer | Operational Concentration | Preferred Range |
| --- | --- | --- |
| sodium cholate | 0.02%-50% | 0.1%-16% |
| sodium dodecyl sulfate | 0.02%-50% | 0.1%-2% |
| sodium deoxycholate | 0.02%-50% | 0.1%-16% |
| taurodeoxycholate | 0.02%-solubility | 0.1%-16% |
| sodium glycocholate | 0.02%-solubility | 0.1%-16% |
| sodium taurocholate | 0.02%-solubility | 0.1%-16% |
| DMSO | 0.02%-solubility | 5%-50% |

4. Suitable Therapeutic Agents

In order for the present invention to operate effectively, it is necessary that the therapeutic agent retained within the mucosal dome be capable of permeating the mucosal membrane either alone or in combination with a suitable permeation enhancer.

The present invention has applicability to a variety of drugs affecting the central nervous system. For example, the present invention may easily be utilized in the administration of opioid agonists (such as fentanyl, alfentanil, sufentanil, lofentanil, and carfentanil), opioid antagonists (such as naloxone and nalbuphene), butyerophenones (such as droperidol and haloperidol); benzodiazepines (such as valium, midazolam, triazolam, oxazolam, and lorazepam); GABA stimulators (such as etomidate); barbiturates (such as thiopental, methohexital, thiamazol, pentobarbital, and hexobarbital); di-isopropylphenols drugs (such as diprivan); and other central nervous system-acting drugs such as levodopa. It will be appreciated that other drugs may also be utilized within the scope of the present invention either singly or in combination.

Table 1 lists some of the CNS-acting drugs which are suitable for incorporation into the mucosal dome of the present invention, as well as some of the characteristics of those drugs.

TABLE 1

| GENERIC DRUG | DRUG CLASS | DOSE RANGE |
| --- | --- | --- |
| methohexital | barbiturate | 10-500 mg |
| pentobarbital | barbiturate | 50-200 mg |
| thiamylal | barbiturate | 10-500 mg |
| thiopental | barbiturate | 50-500 mg |
| fentanyl | opioid agonist | 0.05-5 mg |
| alfentanil | opioid agonist | 0.5-50 mg |
| sufentanil | opioid agonist | 5-500 μg |
| lofentanil | opioid agonist | 0.1-100 μg |
| carfentanil | opioid agonist | 0.2-100 μg |
| naloxone | opioid antagonist | 0.05-5 mg |
| nalbuphene | opioid antagonist | 1-50 mg |
| diazepam | benzodiazepine | 1-40 mg |
| lorazepam | benzodiazepine | 1-4 mg |
| midazolam | benzodiazepine | 0.5-25 mg |
| oxazepam | benzodiazepine | 5-40 mg |
| triazolam | benzodiazepine | 250-1000 mg |
| droperidol | buterophenone | 1-10 mg |
| haloperidol | buterophenone | 0.5-10 mg |
| propanidid | eugenol | 1-10 mg |
| etomidate | GABA stimulator | 5-60 mg |
| propofol | substituted phenol | 3-50 mg |
| ketamine | phencyclidine | 5-300 mg |
| diprivan | substituted phenol | 5-20 mg |

Drugs having effects on the cardiovascular and renal vascular systems may also be administered using a mucosal dome of the present invention. A few examples of such drugs are identified in Table 2.

TABLE 2

| GENERIC DRUG | DRUG CLASS | DOSE RANGE |
| --- | --- | --- |
| Bretylium | antiarrhythmic | 50-500 mg |
| Captopril | ACE inhibitor | 25-75 mg |
| Clonidine | antihypertensive | 0.1-0.5 mg |
| Dopamine | renal vascular | 0.5-5 mg |
| Enalapril | ACE inhibitor | 5-15 mg |
| Esmolol | antihypertensive/angina | 100-250 mg |
| Furosemide | diuretic | 20-100 mg |
| Isosorbide | angina | 2.5-40 mg |
| Labetolol | antihypertensive | 100-400 mg |
| Lidocaine | antiarrhythmic | 50-250 mg |
| Metolazone | diuretic | 5-50 mg |
| Metoprolol | antihypertensive | 25-100 mg |
| Nadolol | antihypertensive | 40-160 mg |
| Nifedipine | antihypertensive/ angina/vasodilator | 10-40 mg |
| Nitroglycerin | antihypertensive/angina | 0.4-1.0 mg |
| Nitroprusside | hypotensive | 10-50 mg |
| Propranolol | antihypertensive/angina | 0.1-50 mg |

In addition to the foregoing, there are many other drugs which can be administered using a mucosal dome of the present invention. Exemplary of such drugs are those identified in Table 3.

TABLE 3

| GENERIC DRUG | DRUG CLASS | DOSE RANGE |
| --- | --- | --- |
| Benzquinamide | antiemetic | 25-100 mg |

TABLE 3-continued

| GENERIC DRUG | DRUG CLASS | DOSE RANGE |
| --- | --- | --- |
| Meclizine | antiemetic | 25–100 mg |
| Metoclopramide | antiemetic | 5–20 mg |
| Prochlorperazine | antiemetic | 5–25 mg |
| Trimethobenzamide | antiemetic | 100–2500 mg |
| Clotrimazole | antifungal | 10–20 mg |
| Nystatin | antifungal | 100,000–500,000 units |
| Carbidopa | antiparkinson | with levodopa 10–50 mg |
| Levodopa | antiparkinson | 100–750 mg |
| Sucralfate | antisecretory | 1–2 grams |
| Albuterol | bronchodilator | 0.8–1.6 mg |
| Aminophylline | bronchodilator | 100–500 mg |
| Beclomethasone | bronchodilator | 20–50 µg |
| Dyphylline | bronchodilator | 100–400 mg |
| Epinephrine | bronchodilator | 200–500 µg |
| Flunisolide | bronchodilator | 25–50 µg |
| Isoetharine | bronchodilator | 170–680 µg |
| Isoproterenol HCl | bronchodilator | 60–260 µg |
| Metaproterenol | bronchodilator | 0.65–10 mg |
| Oxtriphylline | bronchodilator | 50–400 mg |
| Terbutaline | bronchodilator | 2.5–10 mg |
| Theophylline | bronchodilator | 50–400 mg |
| Ergotamine | antimigraine | 2–4 mg |
| Methysergide | antimigraine | 2–4 mg |
| Propranolol | antimigraine | 80–160 mg |
| Suloctidil | antimigraine | 200–300 mg |
| Ergonovine | oxytocic | 0.2–0.6 mg |
| Oxytocin | oxytocic | 5–20 units |
| Desmopressin acetate | antidiuretic | 10–50 µg |
| Lypressin | antidiuretic | 7–14 µg |
| Vasopressin | antidiuretic | 2.5–60 units |
| Insulin | antihyperglycemic | 1–100 units |

In addition to the foregoing drugs, certain macromolecular drugs (such as β-endorphin, enkephalins, brakydinin, aniotensin I, gonadotropic hormones, adreno-corticotropic hormone (ACTH), calcitonin, parathyroid hormone, and growth hormone), polysaccharides (such as heparin), antigens, antibodies, and enzymes may be adapted for transmucosal administration within the scope of the present invention.

When administering a drug with a mucosal dome within the scope of the present invention, the amount of drug used will generally differ from the amount used in more traditional injection and oral administration techniques. Depending upon the lipophilicity of the drug, its potency, the use of permeation enhancers, and the drug's end use, the total concentration of the drug in the mucosal dome may contain up to 50 times more than the amount of drug which would typically be used in an injection, but it may also contain significantly less than the amount used orally, and it may also contain less than the amount used in some intramuscular injections. For purposes of example, Tables 1, 2, and 3 set forth presently contemplated dosage ranges of the drug within the medicament medium which could be typically used.

In summary, it will be appreciated that a wide variety of drugs can be used within the scope of the present invention. At the same time, several benefits are provided. Efficient delivery of the drug is facilitated while at the same time drug degradation is avoided. The drug can also be administered in a dose to effect manner so that the drug effect produced is precisely controlled.

4. Examples of the Present Invention

The following examples are given to illustrate various embodiments which have been made or may be made in accordance with the present invention. These examples are given by way of example only, and it is to be understood that the following examples are not comprehensive or exhaustive of the many types of embodiments of the present invention which can be prepared in accordance with the present invention.

EXAMPLE 1

In this example, insulin was delivered into a laboratory dog's systemic circulation using principles of the present invention. A laboratory dog was given 500 mg of sodium pentothal intravenously for the induction of anesthesia. The intravenous solution was lactated Ringer's solution. The dog was intubated and mechanically ventilated with 100% oxygen to maintain the $pCO_2$ at 35 mm Hg. An 18 gauge Angiocath was placed in the femoral artery. Anesthesia was maintained with halothane at a concentration needed to keep the mean arterial pressure at approximately 100 mm Hg. Five hundred ml of lactated Ringer's solution was given initially to stabilize the animal. An oral retractor was used to gain access to the buccal mucosa.

An insulin solution was prepared by injecting 3 ml of saline into a glass vial containing 60 mg of insulin crystals (24.4 unit/mg, Sigma Chemical Co., St. Louis, Missouri, cat. no. I-5500). The vial was shaken by hand for about 1 minute before 0.3 ml of 0.1 N NaOH solution was injected into the vial. The vial was then shaken by a mixer for about 15 minutes. The insulin concentration was 18 mg/ml (450 U/ml). A quantity of sodium cholate (bile salt) was added into the vial sufficient to make the sodium cholate concentration 8.8%. The pH of the resultant solution was measured by a pH meter and was found to be in the range from 8.3 to 8.6.

A 0.5 mm–1.0 mm thick layer of silicone grease was spread on the base of a diffusion cell to provide the adhesiveness and prevent leakage of the insulin solution. The diffusion cell had an open top through which the insulin solution was added and removed. The area of the cell's open bottom was 1.89 $cm^2$. A flat object was placed under the cheek of the dog to produce a flat buccal area. The diffusion cell was placed on the buccal mucosa very carefully for 15 minutes. The 15 minute waiting time was to permit the silicone grease to settle and fill any gaps between the cell and the buccal mucosa. Failure to give sufficient waiting time could result in a leaking cell.

At time t=0, 2 ml of the insulin solution were pipetted into the cell through the cell's open top. A piece of plastic film was placed on the top of the cell to prevent evaporation of the solvent in the cell solution. Leakage of the solution from the cell did not occur. The diffusion cell was removed when the dog's blood glucose concentration dropped below 40 mg/dl. The buccal area in contact with the insulin solution was rinsed with a large amount of water.

The blood glucose level was monitored by taking blood samples from the arterial line at proper time points identified below. The glucose concentration in the blood samples were determined by the combination of Glucostix (Ames 2628c) and Glucometer (Model 5625, Ames Division, Miles Labs, Inc., Elkhart, Indiana). The standard procedure as described in the user's manual of the Glucometer was followed.

The time points of collecting blood samples were determined as follows: Before introduction of the insulin solution, several (3–5) blood samples were taken over 30 to 120 minutes as a control to provide a baseline for the normal blood glucose level. Immediately after the introduction of the insulin solution, blood samples were taken at about 20 minute intervals to insure that the dog was not injured by hypoglycemia. Following removal of the diffusion cell, blood samples were taken at 15 to 20 minute intervals to observe the recovery of the blood glucose concentration.

Figure 17:
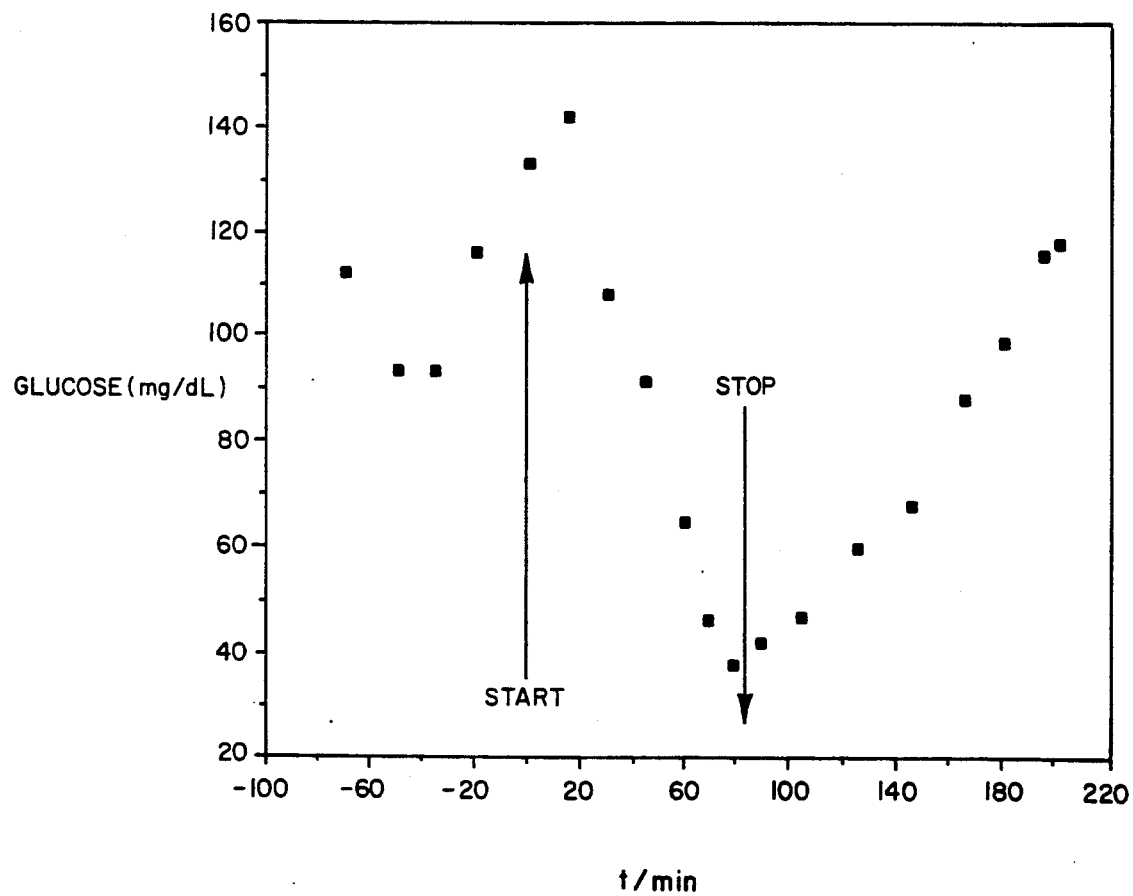
FIG. 17 is a graph of blood glucose (mg/dl) verses time for the transbuccal delivery of insulin illustrating the results of Example 1.

The experimental results of this example are shown graphically in FIG. 17.

EXAMPLES 2-16

In Examples 2-16, insulin was delivered into a laboratory dog's systemic circulation according to the procedure of Example 1, except that different permeation enhancers (bile salts) were used at varying concentrations. Also, in some cases, the surface area of the diffusion cell's open bottom was 0.7 cm$^2$. The experimental results of these examples are shown in Table 4. The bile salts were obtained from Sigma Chemical Co., except for sodium taurocholate, which was obtained from Calbiochem-Behring, Division of American Hoeschst Corp., La Jolla, California.

The term "t(lag)" is defined as the time between the moment the insulin solution is placed in contact with the buccal membrane and when an obvious drop in blood glucose concentration is observed. The term "t(60%)" is defined as the amount of time the insulin solution is in contact with the buccal membrane and when the blood glucose concentration drops below 60% of the average control level.

TABLE 4

| Ex. | Dog No. | Bile Salt | % | t(lag) /min | t(60%) /min | contact area |
|---|---|---|---|---|---|---|
| 2 | 426 | taurocholate | 1.8 | 160 | 260 | 0.7 cm$^2$ |
| 3 | 426 | taurocholate | 4.6 | 120 | 165 | 0.7 |
| 4 | 426 | deoxycholate | 4.6 | 206 | 306 | 0.7 |
| 5 | 426 | glycocholate | 4.6 | 125 | 170 | 0.7 |
| 6 | 426 | glycodeoxycholate | 4.6 | No effect | | 0.7 |
| 7 | 426 | cholate | 4.6 | 162 | 232 | 0.7 |
| 8 | 426 | taurodeoxycholate | 4.6 | 170 | 235 | 0.7 |
| 9 | 503 | taurocholate | 1.8 | 109 | — | 0.7 |
| 10 | 503 | taurocholate | 9.2 | 22 | 35 | 0.7 |
| 11 | 503 | cholate | 9.2 | 30 | 63 | 0.7 |
| 12 | 503 | taurodeoxycholate | 9.2 | 45 | 91 | 0.7 |
| 13 | 513 | taurocholate | 1.8 | No effect | | 0.7 |
| 14 | 513 | deoxycholate | 4.6 | No effect | | 0.7 |
| 15 | 513 | cholate | 9.2 | 30 | 70 | 1.9 |
| 16 | 513 | cholate | 2.3 | 60 | 100 | 1.9 |

EXAMPLE 17

Figure 18:
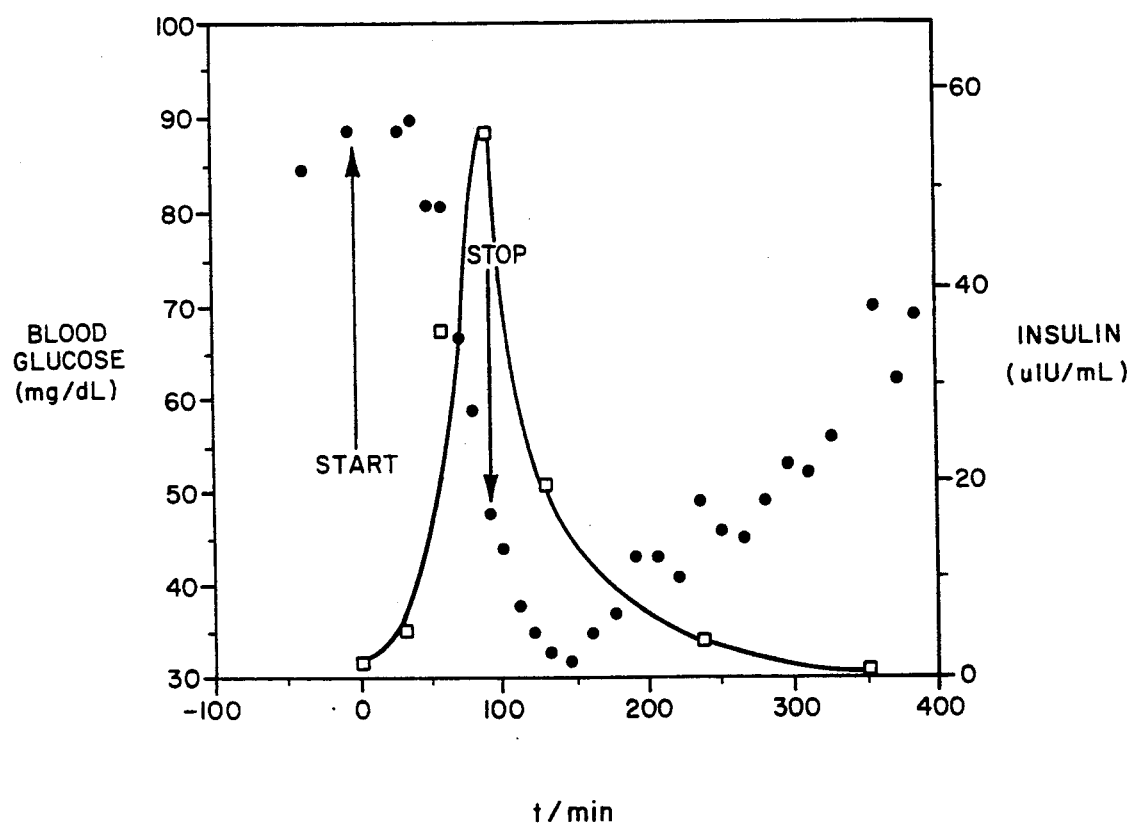
FIG. 18 is a graph of blood glucose (mg/dl) and blood insulin concentration (U/ml) verses time illustrating the results of Example 17.

In Example 17, insulin was delivered into a laboratory dog's systemic circulation according to the procedure of Example 1, except that the insulin concentration was 488 U/ml, the permeation enhancer was 3.0% sodium cholate, and the area of the diffusion cell's open bottom was 2.40 cm$^2$. In addition to the blood glucose tests, radioimmunoassay (RIA) tests were also performed to determine changes in blood insulin level. The RIA assays were performed by the University of Utah Hospital Clinic Laboratories. The results of Example 17 are shown graphically in FIG. 18. FIG. 18 discloses a strong correlation between the rapid blood insulin increase and the rapid blood glucose decrease.

EXAMPLE 18

Figure 19:
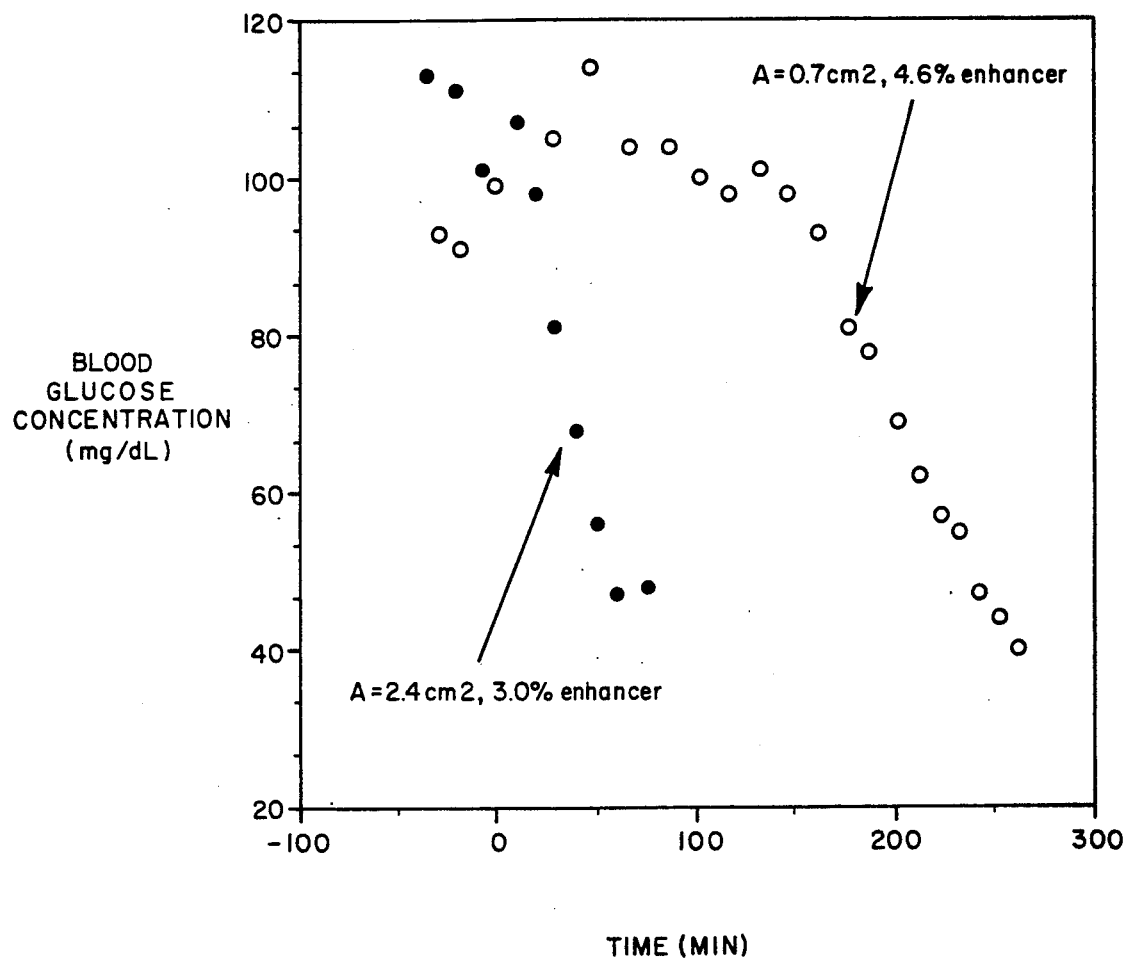
FIG. 19 is a graph of blood glucose (mg/dl) verses time for two diffusion cells having different contacting area which illustrate the results of Example 18.

In Example 18, the effect of contacting area on the transbuccal insulin delivery rate was determined. Insulin was delivered into two different laboratory dog's systemic circulation according to the procedure of Example 1, except that in the first dog the insulin concentration was 488 U/ml, the permeation enhancer was 3.0% sodium cholate, and the area of the diffusion cell's open bottom was 2.40 cm$^2$ and in the second dog the insulin concentration was 488 U/ml, the permeation enhancer was 4.6% sodium cholate, and the area of the diffusion cell's open bottom was 0.7 cm$^2$. The results of Example 18 are shown graphically in FIG. 19. FIG. 19 discloses a dramatic increase in the transbuccal insulin delivery rate when the contact surface area between the insulin solution and the buccal tissue is increased.

EXAMPLE 19

In this example, isoproterenol was delivered into a laboratory dog's systemic circulation using principles of the present invention. A laboratory dog was anesthetized according to the procedure of Example 1. A 50 mg/ml solution of isoproterenol was prepared having a pH of 4.9. Buffered deionized water was used as a donor carrier in 0.7 cm$^2$ diffusion cells attached to the buccal mucosa of an anesthetized dog.

At time t=0, 0.5 ml of the isoproterenol solution was pipetted into the cell through the cell's open top. A piece of plastic film was placed on the top of the cell to prevent evaporization of the solvent in the cell solution. Leakage of the solution from the cell did not occur. The dog's heart rate was monitored over time.

Figure 20:
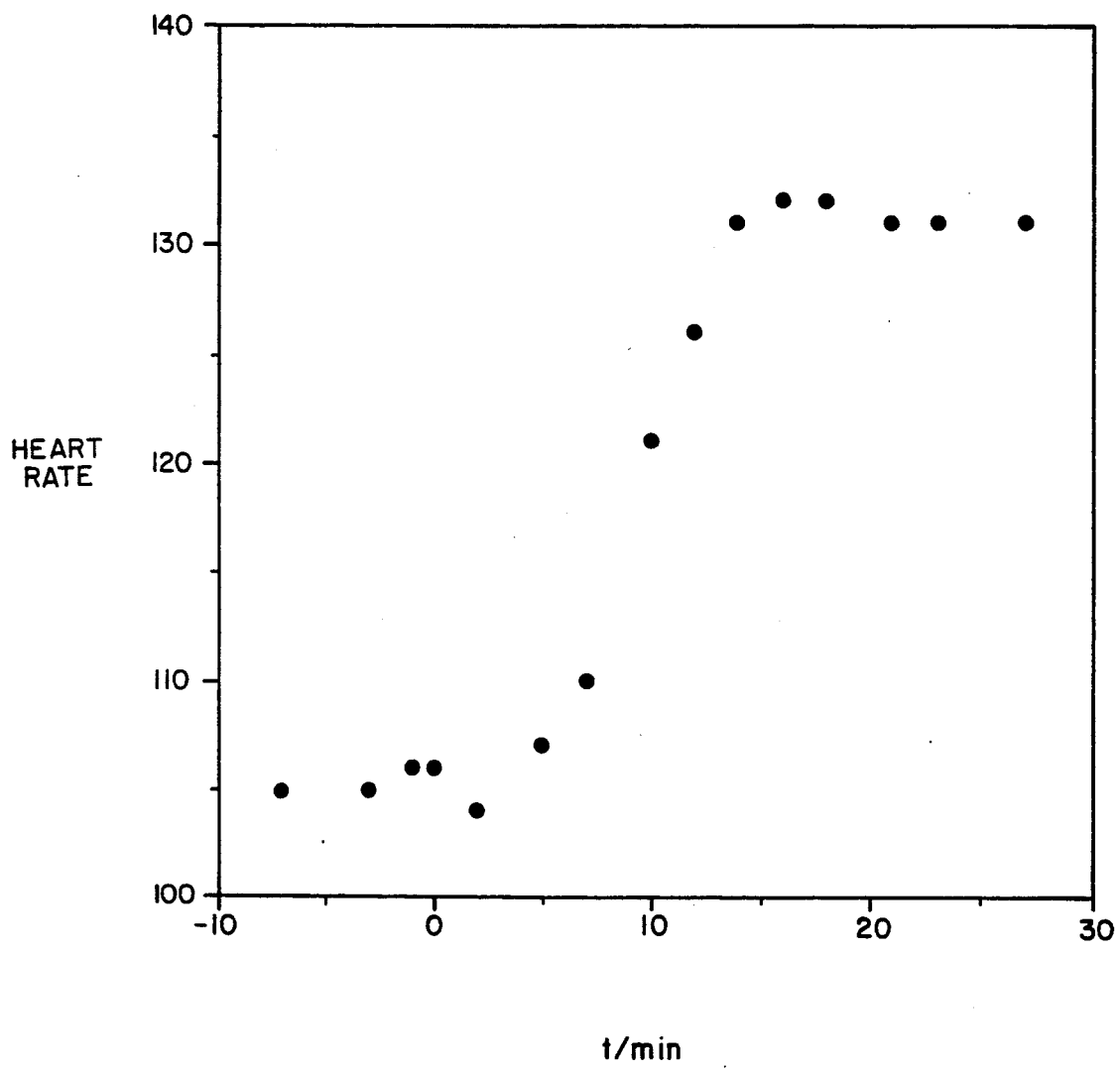
FIG. 20 is a graph of heart rate verses time for the transbuccal delivery of isoproterenol illustrating the results of Example 19.

A significant and rapid increase in the dog's heart rate was observed. The results of Example 19 are illustrated in FIG. 20. From Example 19, it will be appreciated that it is possible to rapidly and transmucosally administer a medicament without the use of a permeation enhancer. In addition, because isoproterenol is 99.98% ionized at a pH of 4.9, the results of Example 19 challenge the conventional theory that only the unionized species can permeate through the buccal mucosa.

EXAMPLE 20

Isoproterenol was delivered into a laboratory dog's systemic circulation according to the procedure of Example 19, except that ethanol was used as a donor carrier. It was found that isoproterenol permeability was increased by a factor of about 40.

EXAMPLE 21

In the procedure of this example, a patient is given an insulin-containing mucosal dome device in order to reduce the patient's blood glucose level. The patient has an initial blood glucose level of 700 mg/dl. A medicament medium containing insulin in a concentration of 300 units/ml is placed within a medicament chamber of the mucosal dome. The medicament medium also contains sodium taurocholate as a permeation enhancer. The sodium taurocholate permeation enhancer has a concentration of 20 mg/ml. The medicament chamber has an opening which is adjusted to have an area of 3 cm$^2$. The mucosal dome is then positioned against a mucosal membrane within the mouth of the patient such that the opening to the medicament chamber is adjacent the mucosal membrane.

After a period of about 20 minutes, the blood glucose level of the patient drops to 100 mg/dl. The mucosal dome is removed from the patient's mouth and discarded.

EXAMPLE 22

An insulin-containing mucosal dome is given to a patient according to the procedure of Example 21, except that after the blood glucose level of the patient drops to 200 mg/dl, the opening to the medicament chamber is adjusted to have an area of 0.5 cm². The patient's blood glucose level remains stable at 150 mg/dl.

EXAMPLE 23-92

In the procedure of Example 23-92, a drug-containing mucosal dome is given to a patient in order to produce a systemic or local effect. A medicament medium containing the drug in a concentration identified in Table 5 is placed within a medicament chamber of the mucosal dome. The medicament chamber has an opening which is adjusted to have an area of 3 cm². The mucosal dome is then positioned against a mucosal membrane within the mouth of the patient such that the opening to the medicament chamber is adjacent the mucosal membrane.

After a period from about 10 to 15 minutes, the desired systemic or local effect is observed. The mucosal dome is removed from the patient's mouth and discarded.

TABLE 5

| Ex. | GENERIC DRUG | DRUG CLASS | DRUG CONCENTRATION |
|---|---|---|---|
| 23 | methohexital | barbiturate | 10–500 mg |
| 24 | pentobarbital | barbiturate | 50–200 mg |
| 25 | thiamylal | barbiturate | 10–500 mg |
| 26 | thiopental | barbiturate | 50–500 mg |
| 27 | fentanyl | opioid agonist | 0.05–5 mg |
| 28 | alfentanil | opioid agonist | 0.5–50 mg |
| 29 | sufentanil | opioid agonist | 5–500 μg |
| 30 | lofentanil | opioid agonist | 0.1–100 μg |
| 31 | carfentanil | opioid agonist | 0.2–100 μg |
| 32 | naloxone | opioid antagonist | 0.05–5 mg |
| 33 | nalbuphene | opioid antagonist | 1–50 mg |
| 34 | diazepam | benzodiazepine | 1–40 mg |
| 35 | lorazepam | benzodiazepine | 1–4 mg |
| 36 | midazolam | benzodiazepine | 0.5–25 mg |
| 37 | oxazepam | benzodiazepine | 5–40 mg |
| 38 | triazolam | benzodiazepine | 250–1000 mg |
| 39 | droperidol | buterophenone | 1–10 mg |
| 40 | haloperidol | buterophenone | 0.5–10 mg |
| 41 | propanidid | eugenol | 1–10 mg |
| 42 | etomidate | GABA stimulator | 5–60 mg |
| 43 | propofol | substituted phenol | 3–50 mg |
| 44 | ketamine | phencyclidine | 5–300 mg |
| 45 | diprivan | substituted phenol | 5–20 mg |
| 46 | bretylium | antiarrhythmic | 50–500 mg |
| 47 | captopril | ACE inhibitor | 25–75 mg |
| 48 | clonidine | antihypertensive | 0.1–0.5 mg |
| 49 | enalapril | ACE inhibitor | 5–15 mg |
| 50 | esmolol | antihypertensive/angina | 100–250 mg |
| 51 | isosorbide | angina | 2.5–40 mg |
| 52 | labetolol | antihypertensive | 100–400 mg |
| 53 | lidocaine | antiarrhythmic | 50–250 mg |
| 54 | metoprolol | antihypertensive | 25–100 mg |
| 55 | nadolol | antihypertensive | 40–160 mg |
| 56 | nifedipine | antihypertensive/angina/vasodilator | 10–40 mg |
| 57 | nitroglycerin | antihypertensive/angina | 0.4–1.0 mg |
| 58 | nitroprusside | hypotensive | 10–50 mg |
| 59 | propranolol | antihypertensive/angina | 0.1–50 mg |
| 60 | dopamine | renal vascular | 0.5–5 mg |
| 61 | benzquinamide | antiemetic | 25–100 mg |
| 62 | meclizine | antiemetic | 25–100 mg |
| 63 | metoclopramide | antiemetic | 5–20 mg |
| 64 | prochlorperazine | antiemetic | 5–25 mg |
| 65 | trimethobenzamide | antiemetic | 100–2500 mg |
| 66 | clotrimazole | antifungal | 10–20 mg |
| 67 | nystatin | antifungal | 100,000–500,000 units |
| 68 | carbidopa | antiparkinson | with levodopa 10–50 mg |
| 69 | levodopa | antiparkinson | 100–750 mg |
| 70 | sucralfate | antisecretory | 1–2 grams |
| 71 | albuterol | bronchodilator | 0.8–1.6 mg |
| 72 | aminophylline | bronchodilator | 100–500 mg |
| 73 | beclomethasone | bronchodilator | 20–50 μg |
| 74 | dyphylline | bronchodilator | 100–400 mg |
| 75 | epinephrine | bronchodilator | 200–500 μg |
| 76 | flunisolide | bronchodilator | 25–50 μg |
| 77 | isoetharine | bronchodilator | 170–680 μg |
| 78 | isoproterenol HCl | bronchodilator | 60–260 μg |
| 79 | metaproterenol | bronchodilator | 0.65–10 mg |
| 80 | oxtriphylline | bronchodilator | 50–400 mg |
| 81 | terbutaline | bronchodilator | 2.5–10 mg |
| 82 | theophylline | bronchodilator | 50–400 mg |
| 83 | ergotamine | antimigraine | 2–4 mg |
| 84 | methysergide | antimigraine | 2–4 mg |
| 85 | propranolol | antimigraine | 80–160 mg |
| 86 | suloctidil | antimigraine | 200–300 mg |
| 87 | ergonovine | oxytocic | 0.2–0.6 mg |

TABLE 5-continued

| Ex. | GENERIC DRUG | DRUG CLASS | DRUG CONCENTRATION |
|---|---|---|---|
| 88 | oxytocin | oxytocic | 5–20 units |
| 89 | desmopressin acetate | antidiuretic | 10–50 μg |
| 90 | lypressin | antidiuretic | 7–14 μg |
| 91 | vasopressin | antidiuretic | 2.5–60 units |
| 92 | insulin | antihyperglycemic | 1–100 units |

5. Summary

In summary, it can be seen that the present invention accomplishes the objects set forth above. The present invention provides apparatus and methods for administering medicaments in order to rapidly induce a desired systemic effect. More particularly, the present invention provides apparatus and methods for administering medicaments which allow for precise control of the medicament dosage to achieve a precise effect of the drug to be administered.

It will also be appreciated that the present invention provides apparatus and methods for the noninvasive administration of a medicament to a patient that avoid the disadvantages of overdosing, underdosing, and the immediate metabolism or inactivation of the digestive system, yet do not involve injection by needle into the patient. Hence, drugs which heretofore had to be administered by invasive methods, may now be safely and rapidly administered noninvasively.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letter Patent is:

1. An apparatus for use in transmucosal delivery of a drug to a patient through the mucosal tissues of the mouth comprising:
    a housing resistant to deformation defining a medicament chamber therein, said chamber having a base which defines at least one opening to said medicament chamber;
    a quantity of medicament medium located within the medicament chamber, said medicament medium comprising a pharmaceutically effective dose of medicament;
    means for temporarily positioning the housing against a mucosal membrane within the mouth, such that the opening to said medicament chamber is positioned over the mucosal membrane and such that the medicament medium within the medicament chamber is capable of contact with the mucosal membrane; and
    means for adjusting the size of the opening to the medicament chamber in order to adjust the exposure of medicament medium within the medicament chamber to the mucosal membrane, the means for adjusting the size of the opening to the medicament chamber comprises:
    a control member having a size and a shape similar to the medicament chamber base and having at least one opening corresponding to the opening of the medicament chamber base, said control member being positioned adjacent the medicament chamber base such that the respective openings of the control member and medicament chamber base are capable of movement with respect to each other; and
    means for moving the control member relative to the medicament chamber base such that the size of the at least one opening to the medicament chamber may be modified by sliding the control member relative to the housing base in order to adjust the exposure of medicament medium within the medicament chamber to the mucosal membrane.

2. An apparatus for use in transmucosal delivery of a drug to a patient through the mucosal tissues of the mouth comprising:
    a housing resistant to deformation defining a medicament chamber therein, said chamber having a base which defines at least one opening to aid medicament chamber;
    a quantity of medicament medium located within the medicament chamber, said medicament medium comprising a pharmaceutically effective dose of medicament;
    means for temporarily positioning the housing against a mucosal membrane within the mouth, such that the opening to said medicament chamber is positioned over the mucosal membrane and such that the medicament medium within the medicament chamber is positioned adjacent the mucosal membrane;
    a substantially flat control member having a size and a shape similar to the medicament chamber base and having at least one opening corresponding to the opening of the medicament chamber base, said control member being positioned adjacent the medicament chamber base such that the respective openings of the control member and medicament chamber base are capable of movement with respect to each other; and
    means for moving the control ember relative to the medicament chamber base such that the size of the at least one opening to the medicament chamber may be modified by sliding the control member relative to the housing base in order to adjust the exposure of medicament medium within the medicament chamber to the mucosal membrane in the range from zero area to the maximum area provided by the opening to the medicament chamber.

3. An apparatus for use in transmucosal delivery of a drug to a patient as defined in claim 2, further comprising holder means secured to the housing, said holder means being configured so as to permit convenient insertion and removal of the apparatus into and out of the mouth of the patient.

4. An apparatus for use in transmucosal delivery of a drug to a patient as defined in claim 3, wherein the holder means extends outside of the mouth.

5. An apparatus for use in transmucosal delivery of a drug to a patient as defined in claim 3, wherein the holder means allows the mouth or teeth of the patient to hold it in position adjacent the mucosal membrane.

6. An apparatus for use in transmucosal delivery of a drug to a patient as defined in claim 3, further comprising means for accessing the medicament chamber such that medicament medium may be introduced into the medicament chamber or removed therefrom.

7. An apparatus for use in transmucosal delivery of a drug to a patient as defined in claim 6, wherein means for accessing the medicament chamber permits medicament medium to be introduced into the medicament chamber or removed therefrom while the housing is positioned against the mucosal membrane.

8. An apparatus for use in transmucosal delivery of a drug to a patient as defined in claim 6, wherein the medicament chamber is reusable by adding new medicament medium to the medicament chamber after each use.

9. An apparatus for use in transmucosal delivery of a drug to a patient as defined in claim 3, wherein the medicament medium further comprises a permeation enhancer capable of increasing the medicament permeability across the mucosal membrane.

10. An apparatus for use in transmucosal delivery of a drug to a patient as defined in claim 9, wherein the permeation enhancer comprises a bile salt.

11. An apparatus for use in transmucosal delivery of a drug to a patient as defined in claim 9, wherein the permeation enhancer comprises a synthetic permeation enhancer.

12. An apparatus for use in transmucosal delivery of a drug to a patient as defined in claim 9, wherein the permeation enhancer comprises a fatty acid.

13. An apparatus for use in transmucosal delivery of a drug to a patient as defined in claim 9, wherein the permeation enhancer comprises a surfactant.

14. An apparatus for use in transmucosal delivery of a drug to a patient as defined in claim 9, wherein the permeation enhancer comprises an organic alcohol.

15. An apparatus for use in transmucosal delivery of a drug to a patient as defined in claim 3, wherein the medicament medium comprises the medicament within a pharmaceutically acceptable carrier.

16. An apparatus for use in transmucosal delivery of a drug to a patient as defined in claim 15, wherein the pharmaceutically acceptable carrier includes water.

17. An apparatus for use in transmucosal delivery of a drug to a patient as defined in claim 3, wherein the medicament medium comprises a hydrogel.

18. An apparatus for use in transmucosal delivery of a drug to a patient as defined in claim 3, wherein the medicament medium comprises a semisolid composition.

19. An apparatus for use in transmucosal delivery of a drug to a patient as defined in claim 3, wherein the medicament medium comprises a sponge-like material saturated with a medicament solution.

20. An apparatus for use in transmucosal delivery of a drug to a patient as defined in claim 3, wherein the medicament is potent and fast-acting.

21. An apparatus for use in transmucosal delivery of a drug to a patient as defined in claim 3, wherein the medicament has effects on the central nervous system of the patient.

22. An apparatus for use in transmucosal delivery of a drug to a patient as defined in claim 3, wherein the medicament has effects on the cardiovascular system of the patient.

23. An apparatus for use in transmucosal delivery of a drug to a patient as defined in claim 3, wherein the medicament has effect on the renal vascular system of the patient.

24. An apparatus for use in transmucosal delivery of a drug to a patient as defined in claim 3, wherein the medicament has effects on the respiratory system of the patient.

25. An apparatus for use in transmucosal delivery of a drug to a patient as defined in claim 3, wherein the medicament is a polypeptide drug.

26. An apparatus for use in transmucosal delivery of a drug to a patient as defined in claim 3, wherein the medicament is a protein drug.

27. An apparatus for use in transmucosal delivery of a drug to a patient as defined in claim 3, wherein the medicament is an opioid agonist.

28. An apparatus for use in transmucosal delivery of a drug to a patient as defined in claim 3, wherein the medicament is an opioid antagonist.

29. An apparatus for use in transmucosal delivery of a drug to a patient as defined in claim 3, wherein the medicament has antiemetic effects.

30. An apparatus for use in transmucosal delivery of a drug to a patient as defined in claim 3, wherein the medicament has antimigraine effects.

31. An apparatus for use in transmucosal delivery of a drug to a patient as defined in claim 3, wherein the medicament has bronchodilator effects.

32. An apparatus for use in transmucosal delivery of a drug to a patient as defined in claim 3, wherein the medicament has oxytocic effects.

33. An apparatus for use in transmucosal delivery of a drug to a patient as defined in claim 3, wherein the medicament has antidiuretic effects.

34. An apparatus for use in transmucosal delivery of a drug to a patient as defined in claim 3, wherein the medicament is insulin.

35. An apparatus for use in transmucosal delivery of a drug to a patient as defined in claim 3, wherein the medicament is fentanyl.

36. An apparatus for use in transmucosal delivery of a drug to a patient as defined in claim 3, wherein the medicament is ergotamine.

* * * * *

UNITED STATES PATENT AND TRADEMARK OFFICE
CERTIFICATE OF CORRECTION

PATENT NO. : 5,122,127
DATED : June 16, 1992
INVENTOR(S) : THEODORE H. STANLEY

It is certified that error appears in the above-identified patent and that said Letters Patent is hereby corrected as shown below:

```
Column 1, line 11, "Brian Hauge," should be --Brian Hague--
Column 1, line 35, "an" should be --and--
Column 6, line 45, "effecting" should be --affecting--
Column 8, line 1, "verses" should be --versus--
Column 8, line 4, "verses" should be --versus--
Column 9, line 12, "substance" should be --substances--
Column 9, line 49, "affects" should be --effects--
Column 10, line 62, "patients mouth" should be --patient's mouth--
Column 11, line 1, "illustrates" should be --illustrate--
Column 11, line 22, "Rotation" should be --rotation--
Column 11, line 63, after "base" insert --.--
Column 13, line 36, "Other criteria" should be --Another criterion--
Column 13, line 37, "include" should be --includes--
Column 15, line 34, "brakydinin" should be --bradykinin--
Column 21, line 39, "Letter Patent" should be --Letters Patent--
Column 22, line 27, "aid" should be --said--
Column 22, line 49, "ember" should be --member--
Column 24, line 29, "effect" should be --effects--
```

Signed and Sealed this

Sixteenth Day of November, 1993

BRUCE LEHMAN

Attest:

Attesting Officer

Commissioner of Patents and Trademarks